United States Patent
Mao et al.

(10) Patent No.: US 11,766,525 B2
(45) Date of Patent: Sep. 26, 2023

(54) INFUSION DEVICE WITH A HYDROPHILIC SINTERED POROUS PLASTIC OR HYDROPHILIC POROUS FIBER AIR STOP FILTER

(71) Applicant: Porex Corporation, Fairburn, GA (US)

(72) Inventors: Guoqiang Mao, Peachtree City, GA (US); Jack Cam Chan, Peachtree City, GA (US)

(73) Assignee: Porex Corporation, Fairburn, GA (US)

( * ) Notice: Subject to any disclaimer, the term of this patent is extended or adjusted under 35 U.S.C. 154(b) by 378 days.

(21) Appl. No.: 16/612,917

(22) PCT Filed: May 15, 2018

(86) PCT No.: PCT/US2018/032668
§ 371 (c)(1),
(2) Date: Nov. 12, 2019

(87) PCT Pub. No.: WO2018/213247
PCT Pub. Date: Nov. 22, 2018

(65) Prior Publication Data
US 2020/0061307 A1    Feb. 27, 2020

Related U.S. Application Data

(60) Provisional application No. 62/508,546, filed on May 19, 2017.

(51) Int. Cl.
*A61M 5/38*     (2006.01)
*A61J 1/14*     (2023.01)
(Continued)

(52) U.S. Cl.
CPC ............ *A61M 5/38* (2013.01); *A61J 1/10* (2013.01); *A61J 1/145* (2015.05); *A61M 5/1411* (2013.01); *A61M 5/165* (2013.01)

(58) Field of Classification Search
CPC ............ A61M 5/38; A61M 5/1411; A61M 2205/7527; A61J 1/145
See application file for complete search history.

(56) References Cited

U.S. PATENT DOCUMENTS

| 5,897,955 A | 4/1999 | Drumheller |
| 7,094,464 B2 * | 8/2006 | Mao .............. G01N 33/521 |
|  |  | 428/319.3 |

(Continued)

FOREIGN PATENT DOCUMENTS

| CN | 1256158 A | 6/2000 |
| CN | 1326366 A | 12/2001 |

(Continued)

OTHER PUBLICATIONS

International Preliminary Report on Patentability, PCT Patent Application No. PCT/US2018/032668, dated Nov. 28. 2019, 11 pages.

(Continued)

*Primary Examiner* — Jenna Zhang
(74) *Attorney, Agent, or Firm* — Kilpatrick Townsend & Stockton LLP

(57) ABSTRACT

The present invention provides infusion devices, such as intravascular (IV) devices, comprising a hydrophilic sintered porous plastic filter or a hydrophilic porous fiber filter which are effective at stopping or greatly reducing transmission of air through the filter.

23 Claims, 7 Drawing Sheets

(51) Int. Cl.
   *A61J 1/10* (2006.01)
   *A61M 5/14* (2006.01)
   *A61M 5/165* (2006.01)

(56) References Cited

U.S. PATENT DOCUMENTS

| | | | | |
|---|---|---|---|---|
| 2004/0015131 | A1* | 1/2004 | Flaherty | A61M 5/38 604/123 |
| 2008/0097315 | A1* | 4/2008 | Miner | A61M 5/1411 604/122 |
| 2010/0294693 | A1* | 11/2010 | Lynn | B65D 27/12 493/227 |
| 2014/0228806 | A1 | 8/2014 | Alisantoso et al. | |
| 2015/0018765 | A1 | 1/2015 | Wong et al. | |
| 2016/0213861 | A1* | 7/2016 | Whitaker | A61M 5/1411 |

FOREIGN PATENT DOCUMENTS

| | | |
|---|---|---|
| CN | 1660453 A | 8/2005 |
| CN | 102688533 A | 9/2012 |
| CN | 103432640 A | 12/2013 |
| CN | 203777404 U | 8/2014 |
| CN | 104274887 A | 1/2015 |
| EP | 1106193 A1 | 6/2001 |
| EP | 1312385 A1 | 5/2003 |
| EP | 1568393 | 8/2005 |
| WO | 2014000494 | 1/2014 |
| WO | 2016123116 | 8/2016 |
| WO | 2016137814 | 9/2016 |

OTHER PUBLICATIONS

Office Action, Chinese Patent Application No. 201880047782.0, Office Action, dated May 31, 2021, 17 pages.
PCT Patent Application No. PCT/US2018/032668, International Search Report and Written Opinion, dated Aug. 24, 2018, 17 pages.
Application No. CN201880047782.0 , Notice of Decision to Grant, dated May 18, 2022, 6 pages.
Office Action, Chinese Patent Application No. 201880047782.0, dated Dec. 21, 2021, 13 pages.

* cited by examiner

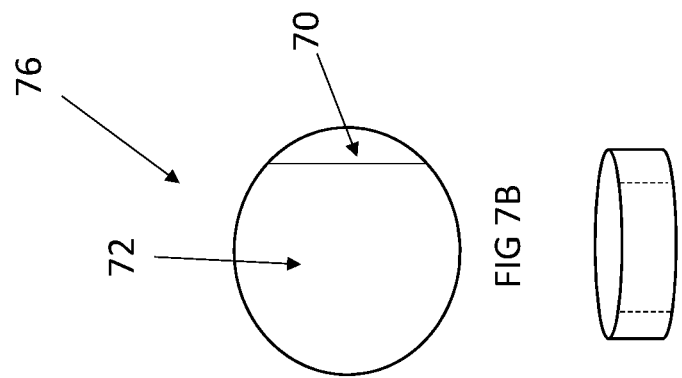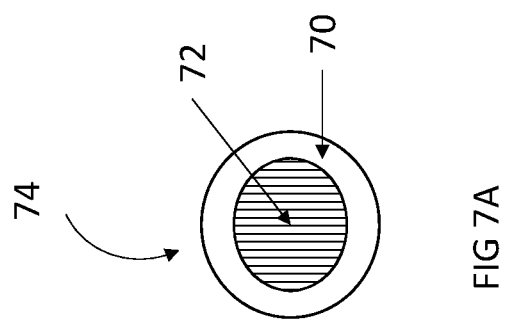
Fig. 7

INFUSION DEVICE WITH A HYDROPHILIC SINTERED POROUS PLASTIC OR HYDROPHILIC POROUS FIBER AIR STOP FILTER

FIELD OF THE INVENTION

The present invention provides infusion devices, such as intravascular (IV) devices, comprising a hydrophilic sintered porous plastic filter or a hydrophilic porous fiber filter which are effective at stopping or greatly reducing transmission of air through the filter.

BACKGROUND

Hospitals and other healthcare facilities often find it necessary to administer fluids to patients through infusion devices. Intravenous delivery can be via what is commonly referred to as an "IV" or an "IV set." These systems often include a delivery bag of saline, an infusion bag, or any other type of specific drug or treatment chemical to be delivered to the patient for the treatment protocol. IV sets generally include a connector for connection to a fluid reservoir or IV bag, a drip chamber used to determine the flow rate of fluid from the fluid reservoir, an intravenous fluid line for providing a connection between the fluid reservoir and the patient, and a catheter that may be positioned intravenously in a patient. An IV set may also include a Y-connector that allows for the piggybacking of IV sets and for the administration of medicine from a syringe into the tubing of the IV set.

It is generally desirable that the IV or catheter delivery be air and bubble free, in order to prevent the introduction of dangerous air bubbles into the patient's system. If air bubbles are allowed to enter a patient's blood stream while receiving administration of liquids, the air bubbles can form an air embolism or otherwise cause serious injury to the patient. It is thus standard practice to remove air from IV sets that access a patient's blood flow or other fluids. However, in spite of the importance of removing air bubbles while priming an IV set for use in the intravenous administration of liquids, the complete removal of air bubbles can be a time consuming and difficult process. There are a number of processes that healthcare personal may use to remove air bubbles from IV sets. However, improvements are desirable.

Currently available IV products such as AirStop from B. Braun Medical Inc. (Bethlehem, Pa.) use polyether sulfone membranes with a pore size of about 15 microns (μm). Similar membranes have been employed by other manufacturers (Becton Dickinson—US Publication Number 2016/0213862). These membrane-based IV products have several major drawbacks such as relatively high cost, relatively low flow rates, inconsistency of flow rates and difficulty incorporating the membranes into IV devices because they are relatively fragile. Membranes used in the prior art are soft and cannot be assembled into a lumen or a cavity. When a prior art membrane is used in an IV kit, the membrane must be laminated to a rigid support or welded to the housing. Otherwise, the membranes could not withstand the liquid pressure or air pressure. Lamination and welding generate variation in filtration efficiencies and increase the cost of the product.

There is a need for improved infusion devices, especially IV devices, employing better air stop filters.

SUMMARY OF THE INVENTION

The present invention addresses this unmet need and provides infusion devices comprising a hydrophilic sintered porous plastic filter or a hydrophilic porous fiber filter which are effective at stopping or greatly reducing transmission of air through the filter. Infusion devices may be used to deliver liquid to any location such as into a vessel, into any body cavity or organ. Intravascular includes intravenous and intra-arterial. For example, liquids may also be delivered, without limitation, into the peritoneal cavity, the abdominopelvic cavity, the gastrointestinal system, the urinary system, the cerebrovascular system, the reproductive system and the respiratory system.

Infusion devices employing a sintered porous plastic filter, a hydrophilic porous fiber filter, or a hydrophilic polyurethane foam filter are effective at stopping or greatly reducing transmission of air through the filter and help to maintain fluid in the infusion line downstream of the filter after the fluid in the infusion bag has emptied, thereby reducing the need to prime the line again when a new bag of fluid is added. Another benefit is that potential transmission of air bubbles into the patient is greatly reduced or eliminated.

The hydrophilic sintered porous plastic filter or hydrophilic porous fiber filter may be used with any infusion device, such as an IV device that can accommodate the filters. These filters may be employed in different locations within an IV device such as within the drip chamber, within the spike, or within a separate component positioned either below or above the drip chamber.

These hydrophilic sintered porous plastic filters and hydrophilic porous fiber filters are self-supporting, relatively rigid and easy to assemble into the IV device, in contrast to prior art membrane filters which are more fragile, not self-supporting and more difficult to stabilize in an IV device.

BRIEF DESCRIPTION OF THE FIGURES

FIG. 7. A schematic representation of sintered porous plastic filters and porous fiber filters having two regions, a hydrophobic region to permit air transfer and a hydrophilic region for liquid filtration and air stop properties. FIG. 7A shows a disk filter containing a central hydrophilic region surrounded by an annular hydrophobic region. FIG. 7B shows a disk filter with a hydrophilic region adjacent to a hydrophobic region.

DETAILED DESCRIPTION OF THE INVENTION

The present invention addresses this unmet need and provides infusion devices, such as IV devices, comprising a hydrophilic sintered porous plastic filter, a hydrophilic porous fiber filter, or a hydrophilic polyurethane foam filter which are effective at stopping or greatly reducing transmission of air through the filter. These hydrophilic sintered porous plastic filters, hydrophilic porous fiber filters, and hydrophilic polyurethane foam filters are relatively rigid, self-supporting, and can be frictionally fit into desired locations within an infusion device or fluid transmission line.

Figure 1:
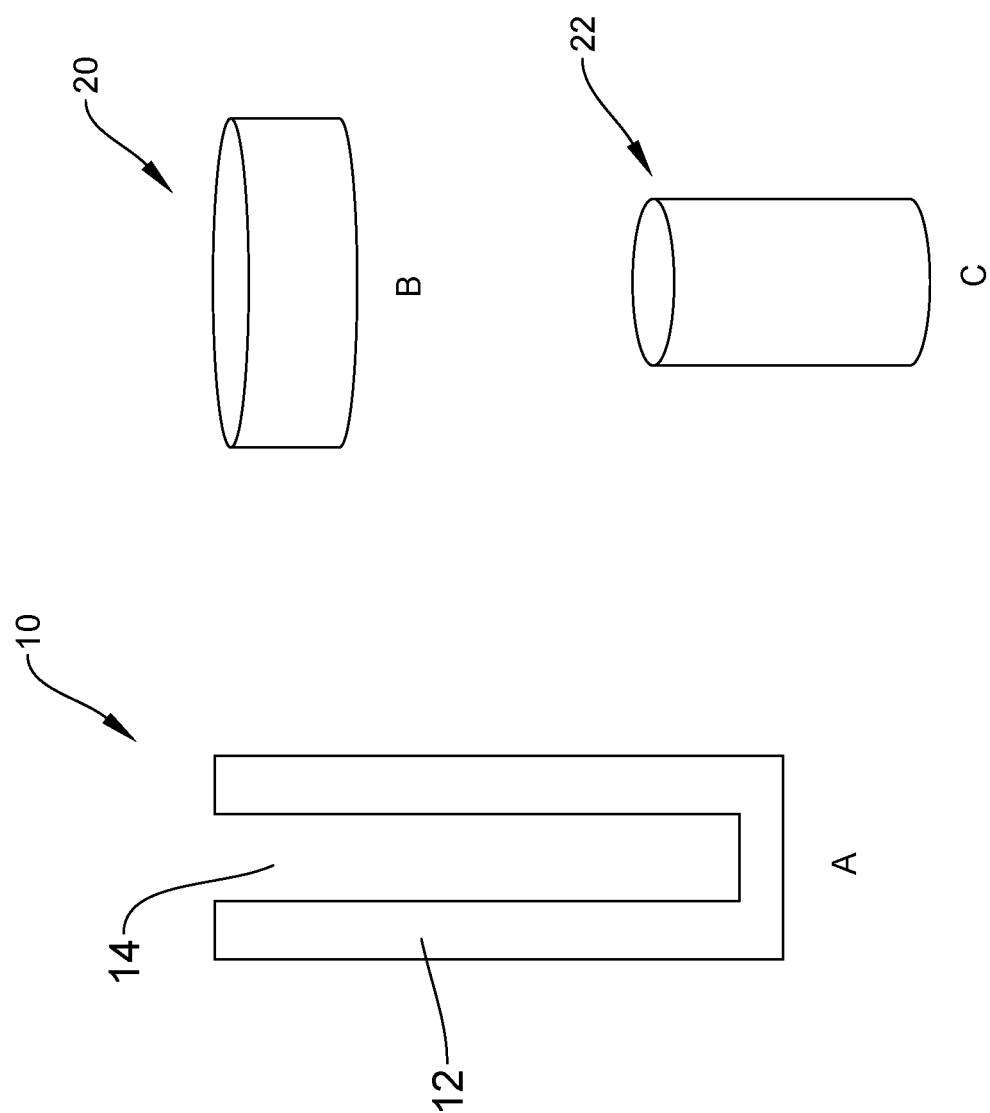
FIG. 1. A hydrophilic sintered porous plastic air stop filter or hydrophilic porous fiber air stop filter in the form of a cylinder with a closed end (A), a disk (B) and a plug (C).

These hydrophilic sintered porous plastic filters, hydrophilic porous fiber filters and hydrophilic polyurethane foam filters may be provided in a variety of shapes such as a disk, rod or hollow tube. FIG. 1A illustrates one example of a filter 10 that defines a cylindrical circumference 12 with a hollow central portion 14. FIG. 1B illustrates one example of a filter 20 that has a disk shape. FIG. 1C illustrates one example of a filter 22 that has a rod shape. Although these specific examples are shown and described, it should be understood that alternate filter shapes are possible and considered within the scope of this disclosure. As described below, the general intent is that the filter shape selected will depend upon the position within the IV set or catheter into which the filter is to be positioned.

As described herein, the terms "infusion", "IV" or "IV set" are used to describe tubing sets that are typically used in the arterial, intravenous, intravascular, peritoneal, and non-vascular administration of any type of fluid to a patient. It should be understood that the filters described herein may be used in any other treatment plan as well, including but not limited, to urinary catheters, cerebral catheters, catheters accessing the peritoneal cavity, abdominopelvic cavity, gastrointestinal system, urinary system, cerebrovascular system, reproductive system, the respiratory system, or any other anatomical system.

Figure 2:
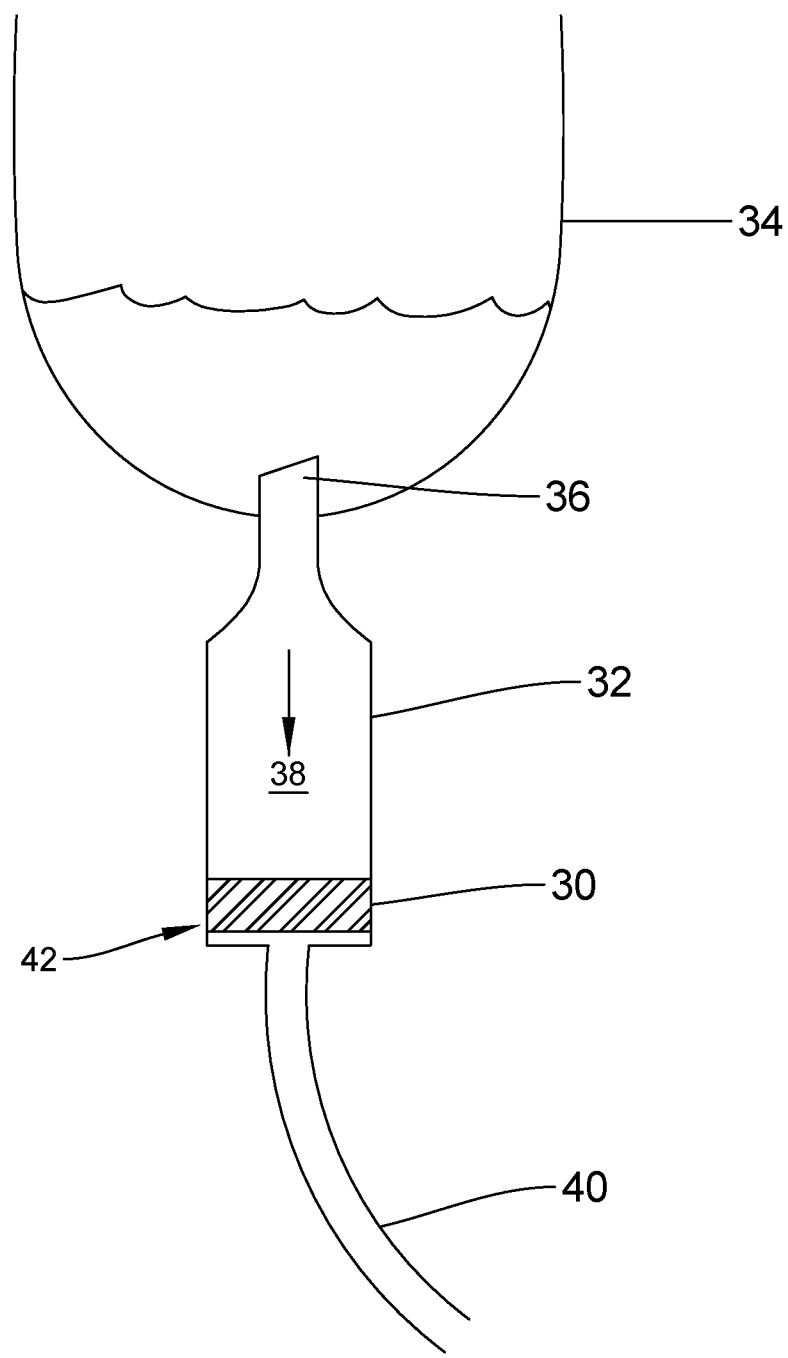
FIG. 2. A schematic representation of an IV fluid reservoir bag, a spike connected to a drip chamber containing a hydrophilic sintered porous plastic air stop filter or hydrophilic porous fiber air stop filter, and an IV tube leading away from the drip chamber. The arrow indicates the path of fluid flow.

As illustrated by FIGS. 2-6, the filters can be frictionally fit into a desired location within an IV device. Such locations include, without limitation, the spike, the viewing chamber or in the downstream tubing, all within the route of liquid flow. For example, FIG. 2 illustrates a filter 30 positioned within a drip chamber 32 of an IV bag 34. Drip chambers 32 are commonly used as part of an infusion system for delivering a fluid to a patient via an intravenous catheter or needle (not shown). Drip chambers 32 are commonly coupled to an IV bag 34 via a spike 36 or any other type of appropriate connection. In this figure, the drip chamber 32 is provided with a spike 36 that punctures the IV bag 34 in order to create liquid flow. The drip chamber 32 defines a reservoir 38 that is configured to receive and store a volume of fluid from the IV bag 34. The volume of fluid collects in reservoir 38 prior to exiting through an intravenous line 40 (that is in communication with or otherwise inserted into a patient, a port, or other fluid delivery device).

As shown, the air filter 30 may be positioned at or near the base 42 of reservoir 12. The air filter 30 is configured to prevent passage of air bubbles from reservoir 38 into intravenous line 40 during an infusion procedure. In some examples, it is possible for the air filter 30 to be retained in place within the reservoir 38 via a filter bracket (not shown). The filter 30 is generally positioned near the bottom portion or base 42 of the reservoir 38 of the drip chamber 32, providing a minimum volume of fluid between air filter 30 and the base 42 of the reservoir 38.

Prior to infusing fluid into a patient, it is common practice to prime drip chamber 32 in order to remove air bubbles from intravenous fluid line 40. However, following the priming procedure, air bubbles may still be trapped at various positions. Agitating or twirling the drip chamber 32 may be unsuccessful in clearing the air bubbles and/or it may dislodge the bubbles. Accordingly, providing air filter 30 within the drip chamber 32 can help to reduce transmission of air bubbles.

Figure 3:
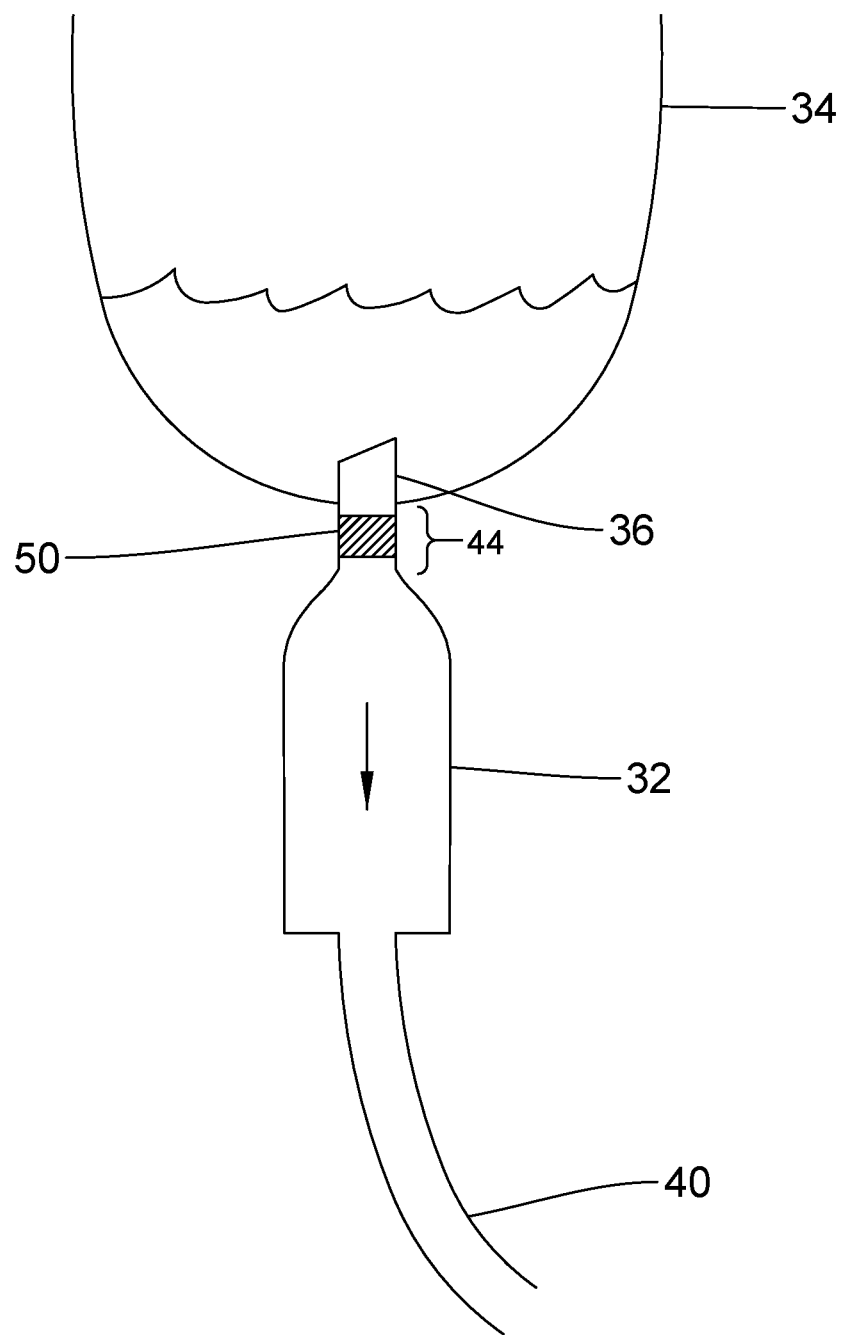
FIG. 3. A schematic representation of an IV fluid reservoir bag, a spike containing a hydrophilic sintered porous plastic air stop filter or hydrophilic porous fiber air stop filter wherein the spike is connected to a drip chamber leading to an IV tube. The arrow indicates the path of fluid flow.

FIG. 3 illustrates a smaller filter 50 that is positioned in the neck 44 of the drip chamber 32. In this example, the filter 50 is positioned just below the spike 36.

Figure 4:
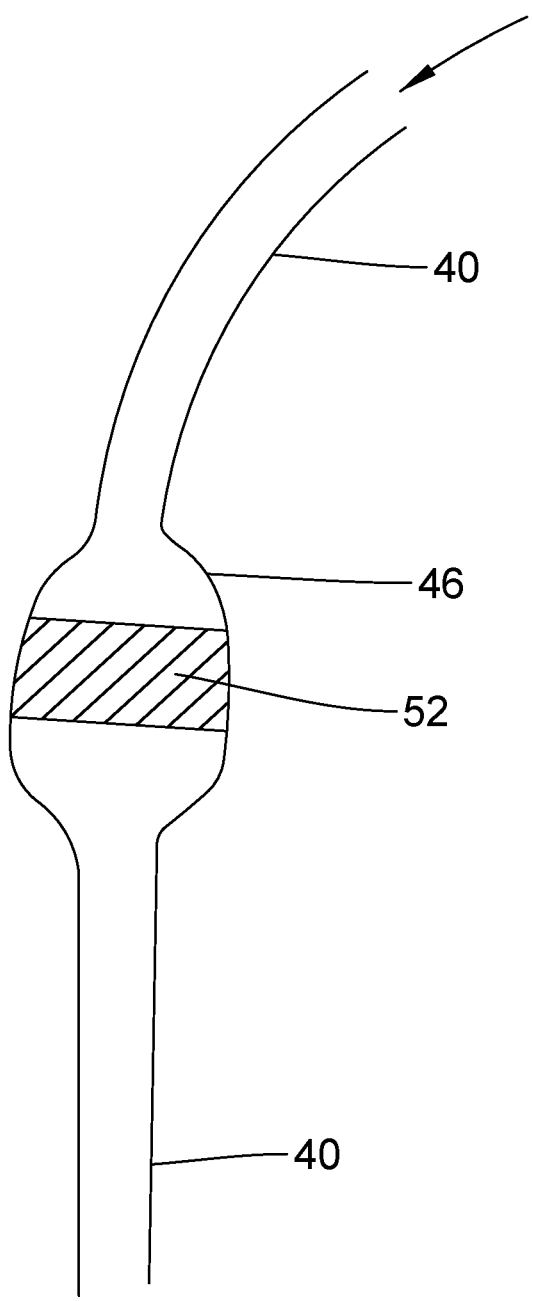
FIG. 4. A schematic representation of an IV tube, an independent inline component connected to the tube and comprising a housing containing a hydrophilic sintered porous plastic air stop filter or hydrophilic porous fiber air stop filter, wherein the inline component is connected to another IV tube leading to a patient. The arrow indicates the path of fluid flow.

FIG. 4 illustrates an independent inline component connected to an intravenous line 40. A housing 46 is positioned along the line 40, and a filter 52 is positioned within the housing 46. In this example, one end of the intravenous line 40 is secured to an IV kit or IV bag and the other end of the line (extending from the housing) leads to the patient.

Figure 5:
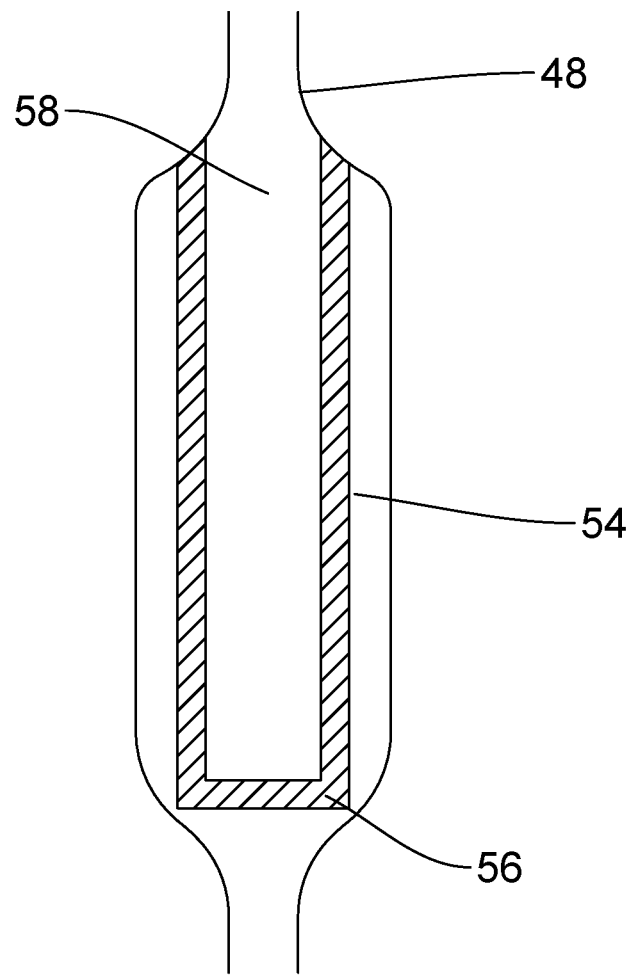
FIG. 5. A schematic representation of an independent inline component comprising a housing containing a cylindrical hydrophilic sintered porous plastic air stop filter wherein the cylindrical filter is closed at one end.

FIG. 5 illustrates an independent in-line component with a similar housing, but shown as an elongated housing 48. Elongated housing 48 supports a cylindrical filter 54. This filter 54 has a first end 56 that defines a closed end 56, and a second end 58 that defines an open end. The open end 58 faces and receives liquid flow. The closed end 56 provides an air stop function. The closed end forms a seal between the downstream and upstream and prevents air from moving from upstream to downstream when liquid runs out.

Figure 6:
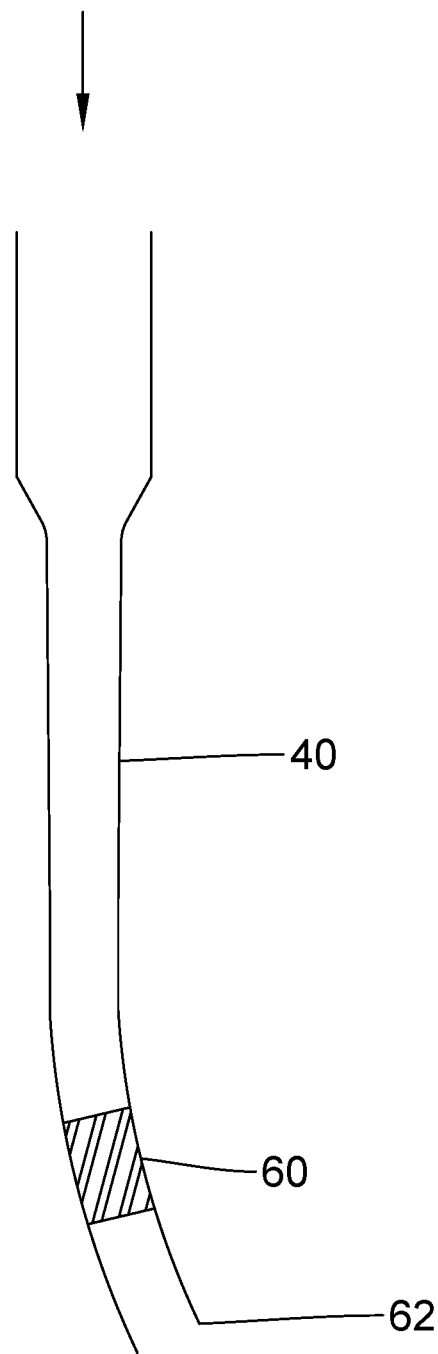
FIG. 6. A schematic representation of an IV kit connected to an IV tube, wherein the IV tube contains a hydrophilic sintered porous plastic air stop filter or hydrophilic porous fiber air stop filter located near the needle end of the IV tube leading to a patient. The arrow indicates the path of fluid flow.

FIG. 6 illustrates a filter 60 positioned toward a needle end 62 of an intravenous tube 40. One end of the intravenous line 40 is secured to an IV kit or IV bag, and the other end of the line leads to the patient.

FIG. 7 illustrates sintered porous plastic filters and porous fiber filters having two regions. In one region, there is a hydrophobic region 70 on at least one portion of the outer perimeter to permit air transfer. The filters are also shown having a hydrophilic region 72 for liquid filtration and air stop properties. FIG. 7A shows a disk filter 74 containing a central hydrophilic region 72 surrounded by an annular hydrophobic region 70. The central hydrophilic region 72 can be frictionally fit into the annular hydrophobic region 70. FIG. 7B shows a disk filter 76 with a hydrophilic region 72 adjacent to a hydrophobic region 70. In this example, the regions 70, 72 may abut one another directly. The hydrophobic region 70 may provide a side sliver of the entirety of the disc filter 76.

As described further below, each of the filters in these examples may be a hydrophilic sintered porous plastic air stop filter, a hydrophilic porous fiber air stop filter or a hydrophilic polyurethane foam air stop filter.

The disclosed filters can also be used as an independent insertion within a housing in any location where it is desired to stop air from travelling through the line, for example close to the entry of the IV line into the patient. In the present context, "independent" means the air stop porous filter is in a housing and can be connected to the IV tubing on site when needed. It could be easily inserted into the IV line or removed from the IV line without affecting the IV kit delivery liquid. These filters may also be used as an in-line filter at any location where the medical professional desires to make a connection to the line.

In contrast to the prior art membranes, these hydrophilic sintered porous plastic filters, hydrophilic porous fiber filters and hydrophilic polyurethane foam filters are self-supporting and can be inserted into a hollow structure without an additional support structure such as a plastic housing or tube. Sintered porous plastic filters and porous fiber filters are not easily bent and retain their original shape under the force of insertion. The sintered porous plastic filters and porous fiber filters used in the present invention have a flexural modulus higher than 1000 psi, higher than 2000 psi or higher than 5000 psi based on the ASTM D790 method at room temperature. This is a significant advantage over the membranes, such as polyether sulfone membranes, used in the IV devices in the prior art.

These sintered porous plastic filters and porous fiber filters provide high particle holding capabilities and filtration throughout their length, as opposed to many prior art filters that provide filtration primarily at their surfaces.

These sintered porous plastic filters and porous fiber filters are also stable for long term storage. Plasma treated sintered porous plastic filters and porous fiber filters coated with positively charged amino acids are safe, have a long shelf life and maintain hydrophilic stability.

Sintered porous plastic filters and porous fiber filters in the present invention are hydrophilic. A water solution with over 60 dynes/cm surface tension can wick into these porous media without application of pressure.

In one embodiment, sintered porous plastic filters and porous fiber filters may have two regions, a hydrophobic region to permit air transfer and a hydrophilic region for liquid filtration and air stop properties. The hydrophobic region provides water intrusion properties at pressures such as over 2 psi. In one embodiment represented in FIG. 7A, the two components may be made separately and then the central component 72 can be inserted into the annular component 70 and frictionally fit. In one embodiment, the hydrophobic region is pure polymer and the hydrophilic region is plasma and solution treated. The filter could be two pieces, the hydrophobic piece and a hydrophilic piece. The hydrophobic region (piece) can be sintered porous polyethylene, PVDF or PTFE and the hydrophilic region (piece) can be sintered polyethylene treated with plasma and solution coating or porous hydrophilic fiber. For example, a round disk filter with a hydrophobic perimeter and hydrophilic internal region. The hydrophilic internal region provides adequate liquid flow and hydrophobic perimeter allows air bubbles to escape from the downstream chamber or line. There are many possible designs and FIG. 7 shows a few examples.

In another embodiment, the sintered porous plastic filters and porous fiber filters may be coated with a membrane for bacterial filtration and air stop properties. Such membrane coated filters may be employed, for example, as an inline filter. In different embodiments, membrane coated sintered porous plastic filters and porous fiber filters possess a particle retention of 1.2 microns 1.0 microns, 0.8 microns, 0.4 microns or 0.2 microns.

The membranes in the present invention is a phase inversion membrane. The phase inversion membrane is formed on the surface of sintered porous plastic filter or porous fiber filter. Phase inversion membrane may be polysulfone, polyethersulfone (PES), polyvinylidene difluoride (PVDF), Nylon, or cellulose acetate.

In one embodiment, these hydrophilic sintered porous plastic filters and hydrophilic porous fiber filters have an average pore size range from about 5 microns to about 20 microns.

In another embodiment, these hydrophilic sintered porous plastic filters and hydrophilic porous fiber filters have a pore volume from 20% to 80%.

In yet another embodiment, these hydrophilic sintered porous plastic filters and hydrophilic porous fiber filters have a liquid flow rate from 1 ml/minute to 20 ml/minute.

In one embodiment, the hydrophilic sintered porous plastic filters and hydrophilic porous fiber filters of the present invention have a bubble point from about 1 psi to about 5 psi. The bubble point is the lowest pressure needed to push air through a water saturated porous matrix.

In various embodiments, the hydrophilic sintered porous plastic filter or the hydrophilic porous fiber filter in the intravascular device can hold a water column downstream of the filter of 6 feet with an average pore size less than 8 microns, 5 feet with an average pore size less than 10 microns, 4 feet with an average pore size less than 14 microns, 3 feet with an average pore size less than 16 microns, less than 2 feet with an average pore size less than 20 microns, and about 6 inches with an average pore size less than 40 microns under dynamic flow conditions.

Sintered porous plastic filters can be made from polyethylene, polypropylene, polyvinylidene difluoride (PVDF), nylons, polyacrylonitrile, polyesters or polystyrene. Polyethylene includes ultrahigh molecular weight polyethylene (UHMWPE), low density polyethylene and high density polyethylene (HDPE).

Fibers which may be used to make the porous fiber filters include without limitation polyolefin fibers, nylon fibers, polyester fibers, cellulose fibers and combinations of these fibers, for example polyethylene (PE) and polyethylene terephthalate (PET). The fibers and fiber products listed in European Patent No. 2,376,683, U.S. Pat. Nos. 6,103,181 and 6,840,692 can be used to make air-stop filters in the present invention.

Sintered porous plastic filters and porous fiber filters are plasma treated to provide them with hydrophilic properties. A preferred plasma is gas plasma which will not generate polymer deposition. The plasma can be air plasma, oxygen plasma, argon plasma, plasma treatment with addition of alcohol, such as methanol, ethanol or isopropanol (IPA), or acids such as acrylic acid, ammonia, or another plasma assist deposition procedure. A plasma assist deposition procedure is a process that deposits a polymer coating on a substrate. It generally consists of evaporating a monomer in a chamber and applying a plasma to polymerize the vapor phase monomer. The monomer or polymerized polymer coats or reacts with the solid substrate. In another embodiment, gas plasma treatment is used.

The plasma treated sintered porous plastic and porous fiber filter are further optionally treated with a solution coating to preserve hydrophilic properties. The solution treatment or coating can be, without limitation, sugar, such as glucose or dextrose; amino acids, such as lysine, arginine, histidine, aspartic acid or glutamic acid; cellulose, such as hydroxyethyl cellulose (HEC); vitamins, such as vitamin A, types of vitamin B, vitamin C, vitamin D, or vitamin E; or water or solutions of water and ethanol mixtures, or combinations thereof.

In one embodiment, all chemicals used in solution treatment are pharmaceutical grade in an IV application.

The hydrophilic plasma treated sintered porous plastic filter and hydrophilic porous fiber filter can be treated with ethanol and preserved in an ethanol solution, such as isopropanol (IPA). Ethanol sterilizes the filter and preserves the hydrophilic properties of the filters.

Sintered porous plastic filters can be made using plastics and methods disclosed in U.S. Pat. Nos. 8,141,717 and 8,920,339.

Porous fiber filters can be made using fibers and methods disclosed in European Patent No. 2,376,683, U.S. Pat. Nos. 6,103,181 and 6,840,692.

Sintered porous plastic filters can be treated to become hydrophilic using methods disclosed in U.S. Pat. No. 7,507,469.

A variety of filter shapes may be employed. In some non-limiting embodiments sintered porous plastic filters may be in the shape of a disk, plug, tube or cylinder. The wall thickness for these filters can be at least 0.5 mm, at least 1 mm, or at least 2 mm to provide the filters with strong air stop properties. The porous fiber filters may be in the shape of a disk, plug or tube with a wall thickness of at least 0.5 mm, at least 1 mm, or at least 2 mm to provide the porous fiber filters with strong air stop properties. In the present invention, the porous plastic filters and porous fiber filters are coated with pharmaceutical grade molecules to provide plasma treated sintered porous plastic or plasma treated porous fiber filters with stable hydrophilicity which are safe for use in IV devices and treatments. These desirable properties and advantages are not taught in the prior art. Pharmaceutical grade molecules, in the present invention, include but are not limited to sugar, such as glucose or dextrose; amino acids, positively charged amino acids, such as lysine, arginine, histidine, aspartic acid or glutamic acid; cellulose, such as hydroxyethyl cellulose (HEC); vitamins, such as vitamin A, types of vitamin B, vitamin C, vitamin D, or vitamin E. These pharmaceutical grade molecules bind to the high surface energy surface (hydrophilic) generated by gas plasma treatment and preserve the surface energy.

Method of Using Hydrophilic Sintered Porous Plastic and Porous Fiber Filter as Air Stop Filter in an Infusion Device In one embodiment, a self-supporting hydrophilic sintered porous plastic or self-supporting hydrophilic porous fiber filter is inserted into an infusion device, such as an IV device, and is frictionally fit into the device. There filters act as an air stop filter to prevent or retard to movement of air through the filter.

In another embodiment, an independent air stop component is connected to an infusion device, such as an IV device, wherein the independent air stop component comprises a hydrophilic sintered porous plastic filter or hydrophilic porous fiber filter and a housing. In this embodiment, the air stop component has two openings with a hydrophilic sintered porous plastic filter or a hydrophilic porous fiber filter located within the housing between the two openings. The two openings are for connection with IV tubing. This device could be used at any location in an IV device by connecting the two opens with the IV tubing The hydrophilic sintered porous plastic or hydrophilic porous fiber filter can be used at different locations in the IV device such as 1 foot, 2 feet, 3 feet, 4 feet, 5 feet, 6 feet, 7 feet, 8 feet, 9 feet or 10 feet from the fluid reservoir based on the pore size or bubble point of the filter subjected to a dynamic fluid column. The flow rate of the filter is affected by the pore size of the filter and the height of the fluid column. A filter's air stop capability depends on the pore size and different pore size filters can be rated for their capabilities of holding a fluid column based on the length of the fluid column. Generally, large pore size filters have a lower capability of holding a fluid column and the fluid will have a higher flow rate through the filter. Smaller pore size filters have a higher capability of holding a fluid column and the fluid will have a lower flow rate through the filter. The fluid column height retained by the filter is between the filter and the patient, in other words downstream of the filter.

In one embodiment, the hydrophilic sintered porous plastic filter or hydrophilic porous fiber filter can be used to control the infusion liquid flow rate. The liquid flow rate depends on the liquid contact surface area of the filter, the liquid column height underneath the filter and the liquid column height above the filter. Once the liquid column height underneath the filter is determined, the flow rate will depend on the filter surface area. The infusion device can be labeled with a preset flow rate. This eliminates or greatly reduces the risk of accidently flooding the patient with liquid which can have severe and detrimental effects on the patient, particularly when medicines are administered in the liquid. In one example, the hydrophilic porous filter can prevent or retard liquid flow and air movement into a downstream target by capillary force.

Although in line use of the filter may slow priming of the system, the priming time may be reduced by squeezing the liquid bag, applying a vacuum on the downstream line, or placing the filter close to the point of entry of the line into the patient.

Sintered hydrophilic porous plastic filters and hydrophilic porous fiber filters can also prevent air bubbles from entering the patient even if a small amount of air gets through the filter. Sintered porous plastic has tortuous pore paths, and these tortuous paths significant reduce the impact of the largest pores on the passage of air. During normal IV conditions, the pressures applied to the filter are water pressure above the filter, the static water column under the filter and liquid flow generated Venturi effect. When the liquid runs out, the pressure above the filter is zero and the filter will significantly reduce the flow rate downstream and reduce the Venturi pressure. With a small amount (less than a small fraction of milliliter) of air passing through the filter at the very beginning, the filter will quickly reduce the Venturi pressure by reducing the downstream liquid flow and blocking air from passing through the filter. With a small amount of air underneath the filter, the air will not continue to move down the IV line and will not be transmitted into patients. As long as the hydrophilic sintered porous plastic filter or the hydrophilic porous fiber filter can withstand the static liquid column, the filter will prevent air from moving into the patient.

The following examples will serve to further illustrate the present invention without, at the same time, however, constituting any limitation thereof. On the contrary, it is to be clearly understood that resort may be had to various embodiments, modifications and equivalents thereof which, after reading the description herein, may suggest themselves to those skilled in the art without departing from the spirit of the invention.

Example 1

Sintered Porous Plastic Filter and Porous Fiber Filter Static Water Column Holding Capability Porous filters in table 1 were inserted into a Fisher brand 5 ml disposable pipette tip with a glass rod. A 1/16 inch inner diameter Tygon® tube was connected to the tip of pipette tip. After the downstream tubing was primed by removing the air and filling with water, and with no water on the top of the filter, pipette tips were raised slowly until the air moved through the filter. The water column heights between the filter and tubing outlet were recorded.

TABLE 1

The static downstream water column height that hydrophilic porous media could hold without air transmitting through the filter.

| Porex Filter | Pore size (microns) | Plasma Treatment | Water column height (inches) |
|---|---|---|---|
| Porex PE/PET Fiber filter | 70 | None | 12 |
| Sintered HDPE | 90 | Oxygen | 8 |
| Sintered UHMWPE | 30 | Oxygen | 20 |
| Sintered UHMWPE | 25 | Oxygen | 24 |
| Sintered UHMWPE | 14 | Oxygen | 88 |

Example 2

Sintered Hydrophilic Porous Plastic Liquid Flow and Air Stop Properties Under Dynamic Downstream Water Column Conditions.

Sintered ultrahigh molecular weight polyethylene (UHMWPE) filters with a 4.75 mm diameter and 4 mm thickness were used for testing. All filters were treated with oxygen plasma to make them hydrophilic. Filters were treated with oxygen plasma (Europlasma, Oudenaarde, Belgium) at 200 watts, 100 mtorr pressure for 20 minutes. The treated filters were inserted into a Fisher brand 5 ml disposable pipette tip with a glass rod. A 1/16 inch inner diameter Tygon® tubing was connected to the tip of the pipette tip and the tube length was adjusted to a desired test length under the filter.

The priming time is the time for the first 5 ml of water to pass through the filter and remove the air from the tubing system. The priming time is longer than the time for the next 5 ml of liquid to pass through the filter. The filter flow rates were measured after the system was primed. The air stop property was observed for the stop of water flow under the filter and air penetration into the filter. The data in Table 2 are the seconds required for 5 ml of deionized water to move through the filter.

TABLE 2

5 ml water priming time (seconds (s)) and 5 ml flow time (seconds (s)) for different pore size hydrophilic sintered porous plastic filters (all UHMWPE)

| Sample number | Pore size (micron)/Pore volume (%) | Downstream length (feet) | 5 ml priming time (s) | 5 ml flow time (s) | Air stop |
|---|---|---|---|---|---|
| 1 | 14/45 | 3 | 126 | 59 | yes |
| 2 | 10/40 | 3 | 180 | 105 | yes |
| 3 | 8/42 | 3 | 270 | 125 | yes |

The results in table 2 indicate that water flow rate is determined by the pore size and pore volume of the sintered hydrophilic porous plastic filter.

TABLE 3

5 ml water flow time (seconds (s)) and air stop properties of sintered porous UHMWPE filters with different downstream tubing lengths.

| Sample number | Pore size (micron)/Pore volume (%) | Downstream length (feet) | 5 ml flow time (s) | Air stop |
|---|---|---|---|---|
| 1 | 14/45 | 3 | 59 | yes |
| 2 | 14/45 | 5 | 45 | no |
| 3 | 10/40 | 3 | 105 | yes |
| 4 | 10/40 | 5 | 76 | yes |
| 5 | 10/40 | 6 | 60 | no |
| 6 | 8/42 | 3 | 125 | yes |
| 7 | 8/42 | 5 | 77 | yes |
| 8 | 8/42 | 6 | 67 | yes |

The results in table 3 indicate that air stop capability is determined by the pore size of the sintered porous plastic filters. The flow rate is determined by the pore size and downstream tubing length

TABLE 4

5 ml priming time (seconds (s)), 5 ml flow time (seconds (s)) and air stop properties of sintered porous UHMWPE filters with different hydrophilic treatments

| Sample number | Pore size/Pore volume (micron/%) | Treatment | Downstream length (feet) | 5 ml priming time (s) | 5 ml flow time (s) | Air stop capability |
|---|---|---|---|---|---|---|
| 1 | 14/45 | Oxygen plasma room temperature 2 weeks | 3 | 126 | 59 | yes |
| 2 | 14/45 | Oxygen plasma treated 55° C. for 1 month | 3 | Fluid did not move, pressure required | 76 | no |
| 3 | 14/45 | Oxygen plasma treated 55° C. for 50 days | 3 | Fluid did not move, pressure required | 76 | no |
| 4 | 14/45 | Oxygen plasma treated, dextrose coated, 55° C. for 1 month | 3 | 190 | 108 | yes |

TABLE 4-continued 5 ml priming time (seconds (s)), 5 ml flow time (seconds (s)) and air stop properties of sintered porous UHMWPE filters with different hydrophilic treatments

| Sample number | Pore size/Pore volume (micron/%) | Treatment | Downstream length (feet) | 5 ml priming time (s) | 5 ml flow time (s) | Air stop capability |
|---|---|---|---|---|---|---|
| 5 | 14/45 | Oxygen plasma treated, dextrose coated, 55° C. for 50 days | 3 | 160 | 106 | yes |
| 6 | 14/45 | Oxygen plasma treated, HEC coated, 55° C. for 1 month | 3 | 218 | 150 | yes |
| 7 | 14/45 | Oxygen plasma treated, HEC coated, 55° C. for 50 days | 3 | 210 | 126 | yes |
| 8 | 14/45 | Oxygen plasma treated, 70% isopropanol (IPA) wetted, 55° C. for 1 month | 3 | 190 | 106 | yes |
| 9 | 14/45 | Oxygen plasma treated, 70% isopropanol (IPA) wetted, 55° C. for 50 days | 3 | 143 | 90 | yes |

Sintered porous plastic filters with dextrose or HEC coating showed good wicking uniformity. The water wicked through the media with a uniform front.

After filters were stored at 55° C. for one month, filters treated with oxygen plasma only showed variation in wicking and liquid had to be pushed through the filter. These filters showed reduced air stop capability. Filters that were plasma treated and coated with dextrose or HEC showed very uniform wicking properties and similar air stop properties. The coated filters showed relatively slow liquid flow rates compared with non-coated filters possibly because the coating reduced the effective pore size of the filters. Sintered porous plastic filters also showed significantly improved hydrophilic stability when they stored wet in a 70% IPA solution. Use of ethanol to store porous plastic filters could prevent bacterial growth in the filters.

Example 3

Sintered Hydrophilic Porous Plastic Filters with Amino Acid Coating and their Properties.

Sintered ultrahigh molecular weight polyethylene (UHMWPE) filters with a 4.75 mm diameter and 4 mm thickness were used for testing. All filters were treated with oxygen plasma (Europlasma, Oudenaarde, Belgium) at 200 watts, 100 mtorr pressure for 20 minutes to make them hydrophilic. The filters were coated with 1% lysine solution by immersing the filters in the solution for 10 minutes. The treated filters were stored in an incubator at 55° C. The treated filters were test at room temperature.

The treated filters were inserted into a Fisher brand 5 ml disposable pipette tip with a glass rod. A 1/16 inch inner diameter Tygon® tubing was connected to the tip of the pipette tip and the tube length was adjusted to a desired test length.

The priming time is the time for the first 5 ml of liquid to pass through the filter and remove the air from the tubing system. The priming time is longer than the time for the sequential 5 ml of liquid to pass through the filter. The filter flow rates were measured after the system was primed by timing how many seconds were required for 5 ml of liquid to pass through the filter. The air stop property was observed for whether there air passed through the filter after the liquid went through the filter.

Table 5 shows water flow rate and air stop properties under different storage conditions for sintered porous plastic filters with an average pore size of about 8 microns and a pore volume of about 42 percent. The liquid flow rate and air stop capability were about the same. This indicates that sintered porous plastic filters treated with oxygen plasma and lysine coating have very stable shelf life as a liquid filter and maintain their air stop capabilities.

TABLE 5

Sintered porous plastic filter with oxygen plasma and lysine treatment storage stability.

| Storage | Time (months) | Downstream tubing height (feet) | Flow rate (ml/min) | Air stop (6 feet) |
|---|---|---|---|---|
| Room temperature | 2 | 6 | 2.1 | yes |
| 55° C. | 1 | 6 | 2 | yes |
| 55° C. | 2 | 6 | 2.2 | yes |
| 55° C. | 3 | 6 | 2.2 | yes |

TABLE 6

The liquid flow rate in grams/minute (g/min) for 0.9% saline solution and deionized water for sintered porous plastic filter with oxygen plasma and lysine treatment.

| Filter | Pore size (microns) | Pore volume (%) | Treatment | Storage | Deionized water flow rate (g/min) | 0.9% Saline flow rate (g/min) | Air-stop height (feet) |
|---|---|---|---|---|---|---|---|
| UHMWPE | 8 | 42 | Oxygen plasma and 1% lysine | 55° C., 2 months | 2.3 | 2.3 | 6 |

Sintered porous plastic filters with oxygen plasma treatment and lysine coating showed the same flow rate for the deionized water and 0.9% saline solution.

TABLE 7

Deionized water flow rates for sintered porous plastic filter with oxygen plasma and lysine treatment after different volume of liquid passed the filter. The flow rate in grams/minute (g/min) was measured after 500 grams, 1000 grams and 2000 grams passed through the filter.

| Filter | Pore size (microns) | Pore volume (%) | Treatment | Storage | Original flow rate (g/min) | Flow rate after 500 grams (g/min) | Flow rate after 1000 grams (g/min) | Flow rate after 2000 grams (g/min) | Down stream tubing height (feet) | Air blocking height (feet) |
|---|---|---|---|---|---|---|---|---|---|---|
| UHMWPE | 8 | 42 | Oxygen plasma and 1% lysine | 55° C., 1 months | 2.2 | 2.1 | 2 | 1.94 | 6 | >6 |
| UHMWPE | 8 | 42 | Oxygen plasma and 1% lysine | 55° C., 2 months | 2.23 | 2.21 | 2.2 | 2.18 | 6 | >6 |
| UHMWPE | 14 | 45 | Oxygen plasma and 1% lysine | 55° C., 2 months | 4.3 | 4.38 | 4.29 | 4.27 | 6 | >5 |

The sintered porous plastic filter with oxygen plasma and lysine treatment showed consistent liquid flow rates after different liquid volumes passed the filter. The filters flow rate will not change if there is no clogging of the filter. The performance of the filter is not affected by the volume of liquid.

All patents, publications and abstracts cited above are incorporated herein by reference in their entirety. It should be understood that the foregoing relates only to preferred embodiments of the present invention and that numerous modifications or alterations may be made therein without departing from the spirit and the scope of the present invention as defined in the following claims.

What is claimed is:

1. An infusion device, comprising:
    an infusion bag;
    a drip chamber defining a reservoir in fluid cooperation with the infusion bag; an infusion line leading from the drip chamber to a patient, the infusion line configured to deliver a fluid or a medicament to the patient; and,
    a plasma treated hydrophilic porous filter is selected from a hydrophilic sintered porous plastic filter or a hydrophilic porous fiber filter and is positioned within the drip chamber reservoir or within the infusion line so that the fluid or the medicament can flow through the filter and so that air is prevented or retarded from moving through the filter,
    wherein the plasma treated hydrophilic porous filter is further treated with a coating comprising pharmaceutical grade molecules to preserve hydrophilic properties of the filter, wherein the coating to preserve hydrophilic properties of the filter comprises positively charged amino acids,
    wherein the plasma treated hydrophilic porous filter is self-supporting without additional support structure, rigid, and is frictionally fit into the drip chamber reservoir or the infusion line.

2. The infusion device of claim 1, wherein the hydrophilic porous filter can prevent or retard air movement into a downstream target by capillary force.

3. The infusion device of claim 1, wherein the hydrophilic porous filter has a liquid flow rate from 1 ml/minute to 20 ml/minute.

4. The infusion device of claim 3, wherein the filter comprises a flexural modulus higher than 1000 psi.

5. The infusion device of claim 3, wherein the filter comprises a flexural modulus higher than 2000 psi.

6. The infusion device of claim 3, wherein the filter comprises a flexural modulus higher than 5000 psi.

7. The infusion device of claim 3, wherein the filter comprises a thickness of at least 0.5 mm.

8. The infusion device of claim 3, wherein the filter comprises a thickness of at least 1 mm.

9. The infusion device of claim 3, wherein the filter comprises a thickness of at least 2 mm.

10. The infusion device of claim 3, wherein the hydrophilic porous filter has an average pore size less than 8 microns and can hold a water column downstream of the filter of 6 feet measured under dynamic flow conditions.

11. The infusion device of claim 3, wherein the hydrophilic porous filter has an average pore size less than 14 microns and can hold a water column downstream of the filter of 4 feet measured under dynamic flow conditions.

12. The infusion device of claim 3, wherein the hydrophilic porous filter has an average pore size less than 40 microns and can hold a water column downstream of the filter of about 6 inches measured under dynamic flow conditions.

13. The infusion device of claim 1, wherein the hydrophilic porous filter is plasma treated with a gas selected from the group consisting of air, oxygen and argon.

14. The infusion device of claim 1, wherein the coating comprises pharmaceutical grade molecules that can provide plasma treated sintered porous plastic or plasma treated porous fiber filters with stable hydrophilicity, which molecules are safe for use in intravenous devices and treatments.

15. The infusion device of claim 1, wherein the hydrophilic porous filter has a pore size from 5 microns to 20 microns and a pore volume from 20% to 80%.

16. The infusion device of claim 1, wherein a liquid with a surface tension over 60 dynes/cm can wick into the hydrophilic porous filter without application of pressure.

17. The infusion device of claim 1, wherein the hydrophilic sintered porous plastic filter is made from a plastic selected from the group consisting of polyethylene, polypropylene, polyvinylidene difluoride, nylon, polyacrylonitrile, polyester and polystyrene.

18. The infusion device of claim 17, wherein the polyethylene is ultrahigh molecular weight polyethylene or high density polyethylene.

19. The infusion device of claim 1, wherein the hydrophilic porous fiber filter is made from polyolefin fibers, nylon fibers, polyester fibers, cellulose fibers or combinations of these fibers.

20. The infusion device of claim 1, wherein the filter is positioned within a housing along the infusion line.

21. The infusion device of claim 1, wherein the infusion device prevents an air bubble from being introduced into the patient by using the infusion device to provide the fluid or the medicament to the patient.

22. The infusion device of claim 1, wherein the amino acids comprise one or more of lysine, arginine, histidine, aspartic acid and glutamic acid.

23. A method of controlling a liquid delivery rate to a patient comprising providing the infusion device of claim 1, choosing a filter size, choosing a filter porosity, selecting a position in the infusion device for placement of the filter and entering a target location of the patient with a needle or a tube connected to the infusion device.

* * * * *